United States Patent [19]
Wachsman

[11] Patent Number: 5,397,442
[45] Date of Patent: Mar. 14, 1995

[54] SENSOR AND METHOD FOR ACCURATELY MEASURING CONCENTRATIONS OF OXIDE COMPOUNDS IN GAS MIXTURES

[75] Inventor: Eric D. Wachsman, Palo Alto, Calif.

[73] Assignee: Gas Research Institute, Chicago, Ill.

[21] Appl. No.: 208,449

[22] Filed: Mar. 9, 1994

[51] Int. Cl.$^6$ .................... G01N 27/26; G01N 30/02; G01N 27/00; H01C 7/00

[52] U.S. Cl. .................... 204/153.16; 204/153.18; 204/153.14; 204/425; 204/426; 204/428; 338/34; 73/23.31; 422/94; 422/98

[58] Field of Search ............... 204/415, 424, 425, 426, 204/427, 428, 153.14, 153.16, 153.18, 410, 412; 338/34; 73/23.31; 422/94, 98

[56] References Cited

U.S. PATENT DOCUMENTS

| | | | |
|---|---|---|---|
| 3,981,785 | 9/1976 | Sandler | 204/195 |
| 4,107,163 | 8/1978 | Donohue | 423/263 |
| 4,276,202 | 6/1981 | Schmidberger et al. | 204/290 R |
| 4,507,643 | 3/1985 | Sunano et al. | 338/34 |
| 4,772,376 | 9/1988 | Yukawa et al. | 204/410 |
| 4,816,800 | 3/1989 | Onaga et al. | 338/34 |
| 4,905,652 | 3/1990 | Nakajima et al. | 123/479 |
| 4,927,517 | 5/1990 | Mizutani et al. | 204/425 |
| 4,950,380 | 8/1990 | Kurosawa et al. | 204/406 |
| 4,988,428 | 1/1991 | Iwakiri et al. | 204/410 |
| 4,990,235 | 2/1991 | Chujo | 204/424 |
| 5,034,112 | 7/1991 | Murase et al. | 204/406 |
| 5,173,166 | 12/1992 | Tomantschger et al. | 204/412 |
| 5,217,588 | 6/1993 | Wang et al. | 204/426 |

Primary Examiner—John Niebling
Assistant Examiner—Bruce F. Bell
Attorney, Agent, or Firm—Hopkins & Thomas

[57] ABSTRACT

Sensors (10, 40) accurately measure the concentration of an oxide compound, such as nitrogen oxide $NO_x$, in a gas mixture (11) which can include oxygen $O_2$. The sensors (10, 40) each comprise a chamber (12, 42) adapted to receive the gas mixture (11) as well as first and second electrochemical cells (16, 17) for consuming oxygen and/or the oxide compound in the chamber (12, 42). The first electrochemical cell (16) comprises a first internal electrode (16a) inside the chamber (12, 42), a first external electrode (16b) outside the chamber (12, 42), and a first electrolyte body (14') therebetween. The second electrochemical cell (17) comprises a second internal electrode (17a) inside the chamber (12, 42), a second external electrode (17b) outside the chamber (12, 42), and a second electrolyte body (14") therebetween. The first and second electrolyte bodies (14', 14") are permeable to oxygen ions. Significantly, the first and second internal electrodes (16a, 17a) are metal oxides having a perovskite lattice structure, which generally exhibit high relative selectivity between oxide compounds, including $NO_x$, and $O_2$. The electrical characteristics of the first and second electrochemical cells (16, 17) are manipulated and/or monitored in order to determine the concentration of $NO_x$ within the chambers (12, 42) and the gas mixture (11).

26 Claims, 9 Drawing Sheets

Temperature programmed reaction of NO and $O_2$ over reduced $La_2CuO_4$.

Temperature programmed reaction of NO and $O_2$ over reduced $LaNiO_3$.

Temperature programmed reaction of NO and $O_2$ over reduced $LaFeO_3$.

Temperature programmed reaction of NO and $O_2$ over reduced $LaCoO_3$.

Temperature programmed reaction of NO and $O_2$ over reduced $LaSrCoO_3$.

Temperature programmed reaction of NO and $O_2$ over reduced $LaRuO_3$.

Temperature programmed reaction of NO and $O_2$ over reduced $LaMnO_3$.

SENSOR AND METHOD FOR ACCURATELY MEASURING CONCENTRATIONS OF OXIDE COMPOUNDS IN GAS MIXTURES

FIELD OF THE INVENTION

The present invention generally relates to sensing specific gases within an environment, and more particularly, to a sensor and method for accurately measuring concentrations of oxide compounds, for example $NO_x$, in gas mixtures, such as exhaust gases and emissions from internal combustion engines or furnaces, via electrochemical reactions.

BACKGROUND OF THE INVENTION

Various apparatus and techniques are known in the art for determining the concentration of oxides of nitrogen ($NO_x$, for example, $N_2O$, $NO$, $NO_2$, etc.), oxides of carbon ($CO_x$, for example, $CO$, $CO_2$, etc.), oxides of sulfur ($SO_x$, for example, $SO_2$, $SO_3$, etc.), and other oxide compounds in a gas mixture, which may include gaseous oxygen ($O_2$), nitrogen ($N_2$), and/or other inert gases. Typically, the electrochemical sensing of oxide compounds has been based on a well known "oxygen pumping principle," which is described briefly hereafter. The oxygen pumping principle has been widely publicized and is described in, for example, U.S. Pat. No. 4,005,001 to Pebler, U.S. Pat. No. 4,770,760 to Noda et al., U.S. Pat. No. 4,927,517 to Mizutani et al., U.S. Pat. No. 4,950,380 to Kurosawa et al., U.S. Pat. No. 5,034,107 to Wang et al. and U.S. Pat. No. 5,034,112 to Murase et al.

Generally, a solid electrolyte conductive to oxygen ions is utilized when employing the oxygen pumping principle. The electrolyte is commonly zirconia ($ZrO_2$), bismuth oxide ($Bi_2O_3$), $ZrO_2$ and/or $Bi_2O_3$ containing alkaline earth dopants, such as calcia (CaO), or containing rare earth dopants, such as yttria ($Y_2O_3$), as a stabilizer, or some other suitable electrolyte having the properties more fully described hereafter. These electrolytes show a high permeability (conductance) to oxygen ions when biased at a constant voltage and when maintained above a certain temperature, for instance, greater than 200° C. in many applications. In other words, in an environment containing oxygen, these electrolytes can selectively permit oxygen to pass therethrough if certain biasing and temperature conditions are met. Said another way, these electrolytes exhibit high conductivity at elevated temperatures, and application of a voltage creates a $O^{2-}$ current or flux.

In sensors utilizing these oxygen-ion-permeable electrolytes, electrodes are usually disposed on opposing sides of the electrolyte, and a voltage is applied across the electrolyte via the electrodes. The electrodes typically comprise platinum (Pt), rhodium (Rh) and/or other noble metals. In this configuration, the combination of the electrodes and the electrolyte disposed therebetween forms an electrochemical cell which is often referred to as a "pumping cell" because it pumps oxygen from the gas mixture exposed to the pumping cell. The pumping cell causes oxygen in the gas mixture to be reduced to oxygen ions at the negative electrode, and then the oxygen ions move through the electrolyte to the positive electrode, where they are oxidized to oxygen again and discharged.

Numerous techniques have been proposed in the art for determining the amount of oxygen and/or oxide compounds in the environment around electrochemical cells, particularly pumping cells, by monitoring the voltage and/or current generated across and/or through the electrolyte. A brief discussion of several exemplary types of prior art sensors is set forth hereafter, but it should be noted that this discussion is not exhaustive.

One type of sensor is described in U.S. Pat. No. 5,217,588 to Wang. This sensor employs two electrochemical cells on a zirconia electrolyte. One cell senses only oxygen gas and the other cell senses all the gases which contain oxygen, including the oxygen gas. Both electrochemical cells are exposed to the same gas mixture, and the difference between the sensed signals is a measure of the concentration of $NO_x$ in the gas mixture.

Another type of sensor is described in U.S. Pat. No. 5,034,112 to Murase et al. In this sensor, a catalyst for reducing $NO_x$ is placed on an electrolyte adjacent to a pumping cell. A current is induced in the pumping cell so as to control the oxygen concentration in the environment around the pumping cell. When the oxygen concentration is depleted to a predetermined level, the catalyst supposedly begins to deplete $NO_x$, and the oxygen concentration of $NO_x$ is determined by measuring the current supplied to the pumping cell.

Although the sensors of the prior art have some merit, they do not provide for highly accurate measurement of $NO_x$ or other oxide compounds in gas mixtures because the electrodes utilized for the electrochemical cells do not provide for sufficient selectivity between oxygen and oxide compounds, particularly $NO_x$. In other words, some amounts of oxygen and some amounts of these oxide compounds are undesirably consumed by the wrong electrode, and this phenomenon results in inaccurate measurements of oxygen as well as oxide concentrations. Moreover, if the gas mixture contains a relatively low oxide concentration as compared with that of oxygen, the signal-to-noise ratio is small, and an accurate determination of the oxide concentration is even more difficult. In exhaust gases or emissions produced by internal combustion engines or furnaces, the concentration of oxygen is typically several thousand times higher than the $NO_x$ concentration. Hence, measurements of $NO_x$ in exhaust gases using the prior art techniques are undesirably and unavoidably inaccurate.

SUMMARY OF THE INVENTION

Therefore, an object of the present invention is to overcome the deficiencies and inadequacies of the prior art as noted above and as generally known in the art.

Another object of the present invention is to provide a sensor and method for accurately determining concentrations of oxide compounds, including but not limited to, $NO_x$, within a gas mixture.

Another object of the present invention is to provide a sensor and method for accurately measuring the concentration of oxide compounds, including but not limited to, $NO_x$, in exhaust gases or emissions produced by internal combustion engines or furnaces.

Another object of the present invention is to provide a sensor and method for accurately measuring the concentration of oxide compounds, including but not limited to, $NO_x$, in environments having a large disparity between oxygen and oxide concentrations.

Another object of the present invention is to provide a method for increasing the signal-to-noise ratio in a sensor for measuring the concentration of oxide compounds, including but not limited to, $NO_x$, in an environment containing gaseous oxygen and/or nitrogen.

Another object of the present invention is to provide electrodes for sensors which are highly selective to oxide compounds, such as $NO_x$, and to $O_2$.

Briefly described, the present invention provides for a sensor and associated method for measuring concentrations of oxide compounds, particularly $NO_x$, in a gas mixture, which may include high amounts of gaseous oxygen $O_2$ and/or nitrogen $N_2$, by using electrochemical reactions. The sensor comprises a chamber adapted to receive the gas mixture and first and second electrochemical cell means situated within the chamber. In a first embodiment of the sensor, the chamber comprises an enclosure for housing the first and second internal electrodes and a pin-like aperture through which the gas mixture enters the enclosure. In a second embodiment of the sensor, the chamber comprises an elongated tube-like enclosure for housing the first and second internal electrodes. The enclosure has first and second apertures for receiving and expelling the gas mixture respectively. Moreover, the first and second internal electrodes are disposed in succession along an axis connecting the first and second apertures, and the first internal electrode is disposed along the axis between the first aperture and the second internal electrode.

In both the first and second embodiments of the sensor, the first electrochemical cell means has a first internal electrode inside the chamber, a first external electrode outside the chamber, and a first electrolyte body between these electrodes. Moreover, the second electrochemical cell means has a second internal electrode inside the chamber, a second external electrode outside the chamber, and a second electrolyte body between these electrodes. The first and second electrolyte bodies are permeable (exhibit high conductivity) to oxygen ions when electrically biased and preferably comprise zirconia ($ZrO_2$), bismuth oxide ($Bi_2O_3$), and/or some other suitable ion-permeable material.

In accordance with a significant feature of the present invention, either one or both of the first and second internal electrodes comprises a metal oxide compound, particularly a perovskite, which is a compound having a perovskite lattice structure. Perovskites have been discovered by the inventors herein to be particularly suited to discriminating between oxygen and a variety of oxide compounds when used as electrodes in electrochemical cells. In other words, a perovskite can be used to consume oxygen without consuming an appreciable amount of an oxide compound, such as $NO_x$, and vice versa.

The operation of the first and second embodiments of the sensor depends upon the materials used for the first and second internal electrodes. The first embodiment can operate in any of three modes, denoted first, second, and third modes, whereas the second embodiment can operate in only the first and second modes, as set forth hereafter. In a first mode of operation, the first internal electrode is the perovskite $La_2CuO_4$ (most preferred), $LaNiO_3$, $LaFeO_3$, $LaCoO_3$, $LaMnO_3$, or $LaSrCoO_3$, any of which is highly selective to oxygen, and the second internal electrode is the perovskite $LaRuO_3$ (most preferred) or $LaMnO_3$, each of which is highly selective to $NO_x$. In a second mode of operation, the second internal electrode comprises any material which can concurrently consume both $NO_x$ and $O_2$, for example but not limited to, $LaMnO_3$, Pt, Rh, or another noble metal, while the first internal electrode comprises the perovskite $La_2CuO_4$ (most preferred), $LaNiO_3$, $LaFeO_3$, $LaCoO_3$, $LaMnO_3$, or $LaSrCoO_3$. In a third mode of operations the first internal electrode comprises any material which can consume both $NO_x$ and $O_2$, for example but not limited to, $LaMnO_3$, platinum, rhodium, or another noble metal, while the second internal electrode comprises the perovskite $La_2CuO_4$ (most preferred), $LaNiO_3$, $LaFeO_3$, $LaCoO_3$, $LaMnO_3$, or $LaSrCoO_3$.

In the first mode of operation, a potential difference is created between the first internal and external electrodes so that the oxygen is removed from the chamber by the first cell means and, after substantially all of the oxygen is removed from the chamber, an electrical characteristic (voltage, current, power, etc.) of the second internal and external electrodes of the second cell means is measured. It should be noted that $LaRuO_3$ is particularly selective to $NO_x$ after depletion of oxygen in the surrounding area. The electrical characteristic corresponds proportionally to the concentration of the oxide compound in the gas mixture. Importantly, because of the high selectivity of the perovskites with respect to oxygen and the oxide compound, a highly accurate measurement of the oxide compound is realized.

In the second mode of operation, a potential difference is created between the first internal and external electrodes so that the oxygen is removed from the chamber by the first cell means. The second internal electrode concurrently consumes both the oxygen and the oxide compound. First and second electrical characteristics associated with the first and second cell means are measured and the concentration of the oxide compound in the gas mixture is determined by mathematically combining, or determining the difference between, the first and second electrical characteristics.

In the third mode of operation, a potential difference is created between the first internal and external electrodes so that both oxygen and the oxide compound are removed concurrently from the chamber by the first cell means. The second internal electrode consumes only oxygen. First and second electrical characteristics associated with the first and second cell means are measured and the concentration of the oxide compound in the gas mixture is determined by mathematically combining, or determining the difference between, the first and second electrical characteristics.

There are many other advantages of the present invention, as set forth hereafter.

An advantage of the present invention is that a number of different oxide compounds may be concurrently measured and monitored in a gas mixture with a high level of precision.

Another advantage of the present invention is that the sensors and their metal oxide constituents are suitable for use as described herein over a wide range of temperatures and in a wide variety of harsh environments.

Another advantage of the present invention is that the sensors and their metal oxide constituents are reliable.

Another advantage of the present invention is that the sensors and their metal oxide constituents are efficient in operation.

Another advantage of the present invention is that metal oxides and particularly perovskites are easily and inexpensively produced in a commercial setting.

Other features, objects, and advantages of the present invention will become apparent to one of skill in the art upon examination of the following drawings and detailed description.

BRIEF DESCRIPTION OF THE DRAWINGS

The present invention can be better understood with reference to the following drawings. The drawings are not necessarily to scale emphasis instead being placed upon clearly illustrating principles of the present invention.

DETAILED DESCRIPTION OF THE PREFERRED EMBODIMENTS

Figure 1:
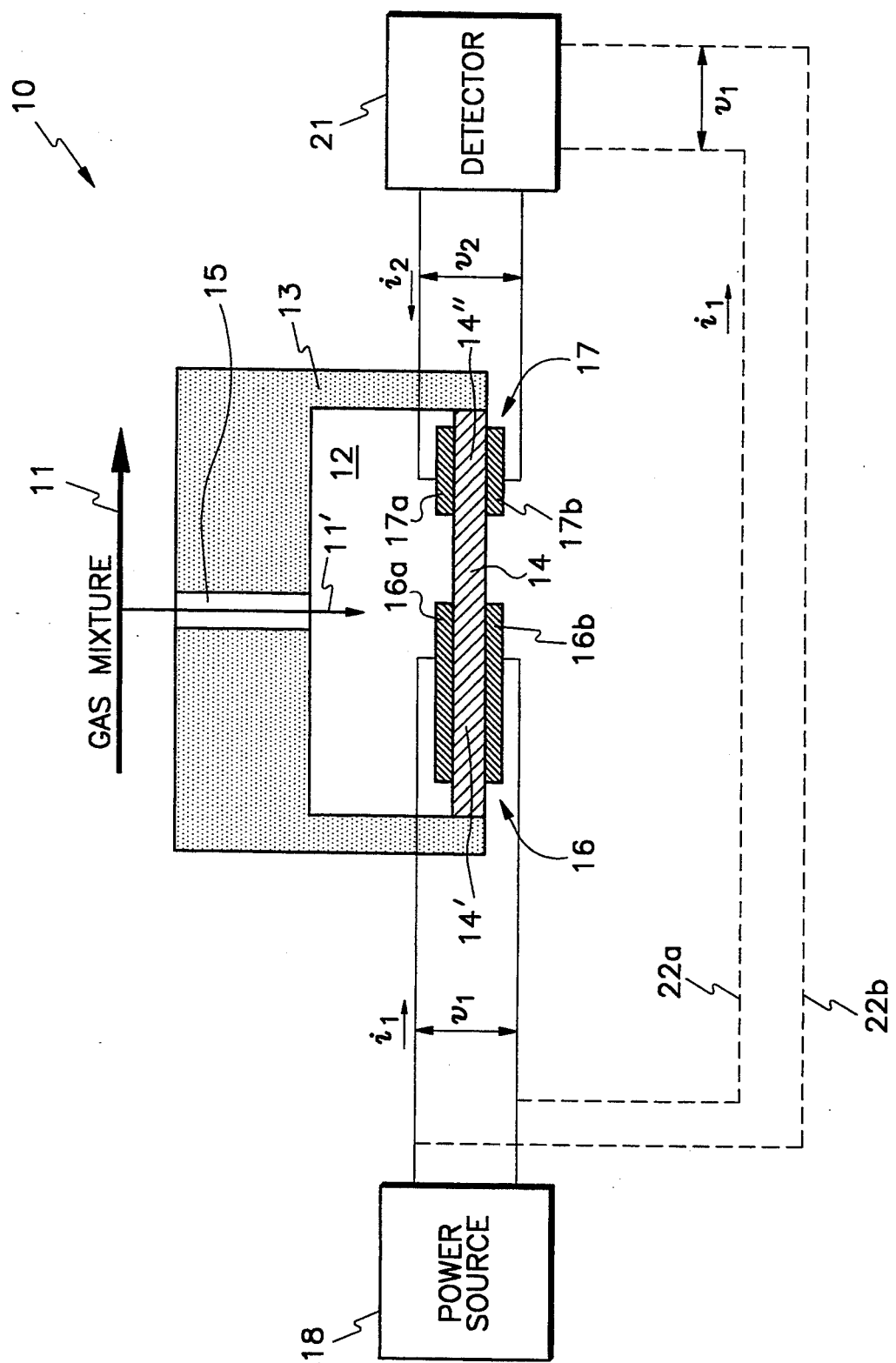
FIG. 1 is a schematic view illustrating a first embodiment of a sensor in accordance with the present invention.

Referring now to the drawings wherein like reference numerals designate corresponding parts throughout the several views, a sensor 10 of FIG. 1 is disposed in a stream of a gas mixture 11, such as exhaust or emissions from an engine or furnace, for accurately and reliably measuring the concentration of oxide compounds, including but not limited to, $NO_x$.

Architecturally, the sensor 10 comprises an enclosed internal chamber 12 of any geometric shape substantially defined by a housing 13 and a solid electrolyte 14 which is permeable to $O_2$ ions, an elongated pin-like aperture 15 for permitting passage of a gas portion 11' of the gas mixture 11 into the chamber 12, a first electrochemical cell 16 for consuming $O_2$ and/or $NO_x$ in the chamber 12 and defined by internal and external electrodes 16a, 16b in combination with an electrolyte body 14' disposed between the electrodes 16a, 16b, and a second electrochemical cell 17 for consuming $O_2$ and/or $NO_x$ within the chamber 12 and defined by internal and external electrodes 17a, 17b in combination with an electrolyte body 14" disposed between the electrodes 17a, 17b.

In the preferred embodiment, for simplicity, the electrolyte bodies 14', 14" are merely different material portions of a singular layer of electrolyte 14. The electrolyte 14 may comprise zirconia ($ZrO_2$), bismuth oxide ($Bi_2O_3$), one or both of the foregoing compounds optionally with one or more dopants, such as calcia (CaO) or yttria ($Y_2O_3$) as a stabilizer, or some other suitable oxygen-ion-permeable electrolyte material. Furthermore, the electrolyte bodies 14', 14" have an ion permeable response defined by the potential differences $v_1$, $v_2$ or currents $i_1$, $i_2$ between respective electrodes 16a, 16b and 17a, 17b of the corresponding first and second electrochemical cells 16, 17.

The amount of gas mixture 11 sampled by the sensor 10 is limited by diffusion through the elongated pin-like aperture 15. The voltages $v_1$, $v_2$ and the currents $i_1$, $i_2$ are affected by the partial pressure of $O_2$ and $NO_x$ at the surface of the internal electrodes 16a, 17a, respectively, and by the diffusion rate of the gases through the pin-like aperture 15. Furthermore, by applying an electrical bias, or potential difference, across electrodes 16a, 16b with the power source 18, the voltage $v_1$ and the current $i_1$ may be increased to thereby increase the rate at which $O_2$ and/or oxide compounds are removed at the surface of the internal electrode 16a.

In accordance with a significant feature of the present invention, the sensor 10 of FIG. 1 is equipped with very highly selective internal electrodes 16a, 17a. Much experimentation was performed by the inventors to find materials that exhibit high relative selectivity between $O_2$ and $NO_x$. The experimentation indicates that metal oxide compounds, and particularly, metal oxide compounds having a perovskite lattice structure, are very selective to particular gaseous oxide compounds, or in other words, are highly active in reacting with particular gaseous oxide compounds. In the context of this document, a "metal oxide" or "metal oxide compound" means a compound having an elemental metal combined with $O_2$. "Perovskite lattice structure" means a lattice structure having two different metals combined with oxygen, or $ABO_x$, where A and B are different metals and where x is any number, but preferably approximately 3. Further, a "perovskite" means any compound having, at least, a perovskite lattice structure.

By extensively examining metal oxide compounds, particularly perovskites, it was determined that the relative selectivity between NO and $O_2$ exhibited by perovskites depends upon the metal oxide chemistry AB in the perovskites $ABO_x$, and that this difference in selectivity can be used to significantly increase the selectivity of gaseous oxide sensors. The following perovskites were determined to be highly selective to $O_2$ and not $NO_x$, while in the presence of both of these gaseous compounds: lanthanum copper oxide ($La_2CuO_4$), lanthanum nickel oxide ($LaNiO_3$), lanthanum iron oxide ($LaFeO_3$), lanthanum cobalt oxide ($LaCoO_3$), and lanthanum strontium cobalt oxide ($LaSrCoO_3$). These results are illustrated in FIGS. 2 through 7.

Figure 2:
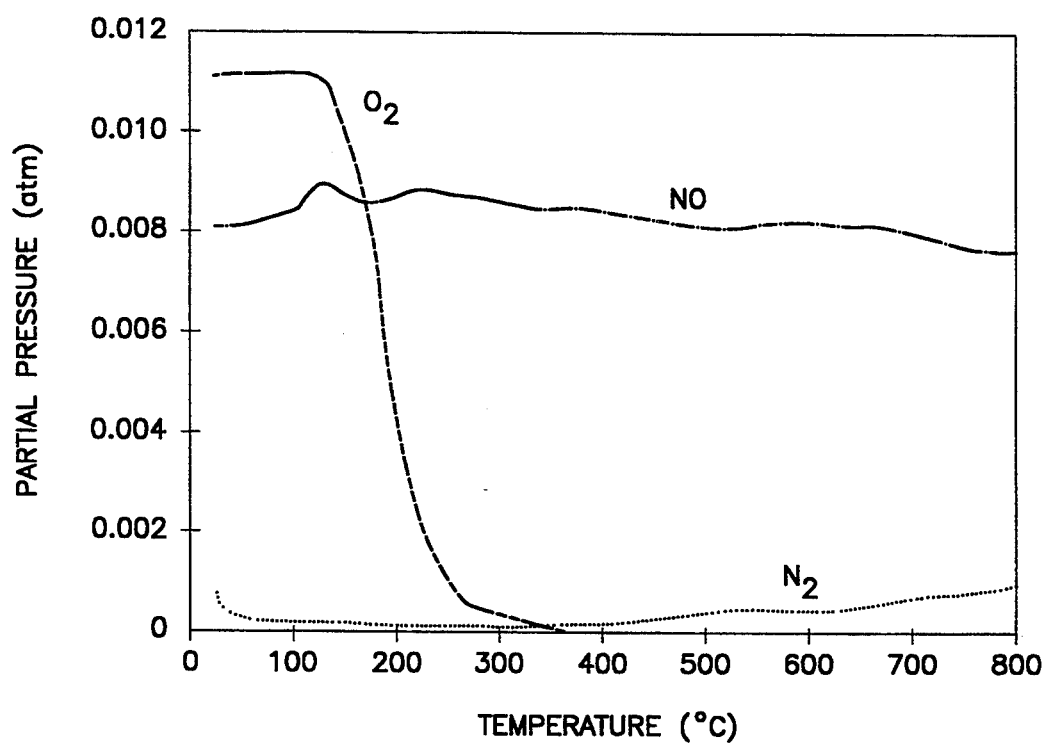
FIG. 2 is a graph of partial pressure versus temperature illustrating a temperature programmed reaction of NO and $O_2$ over reduced $La_2CuO_4$.
Figure 3:
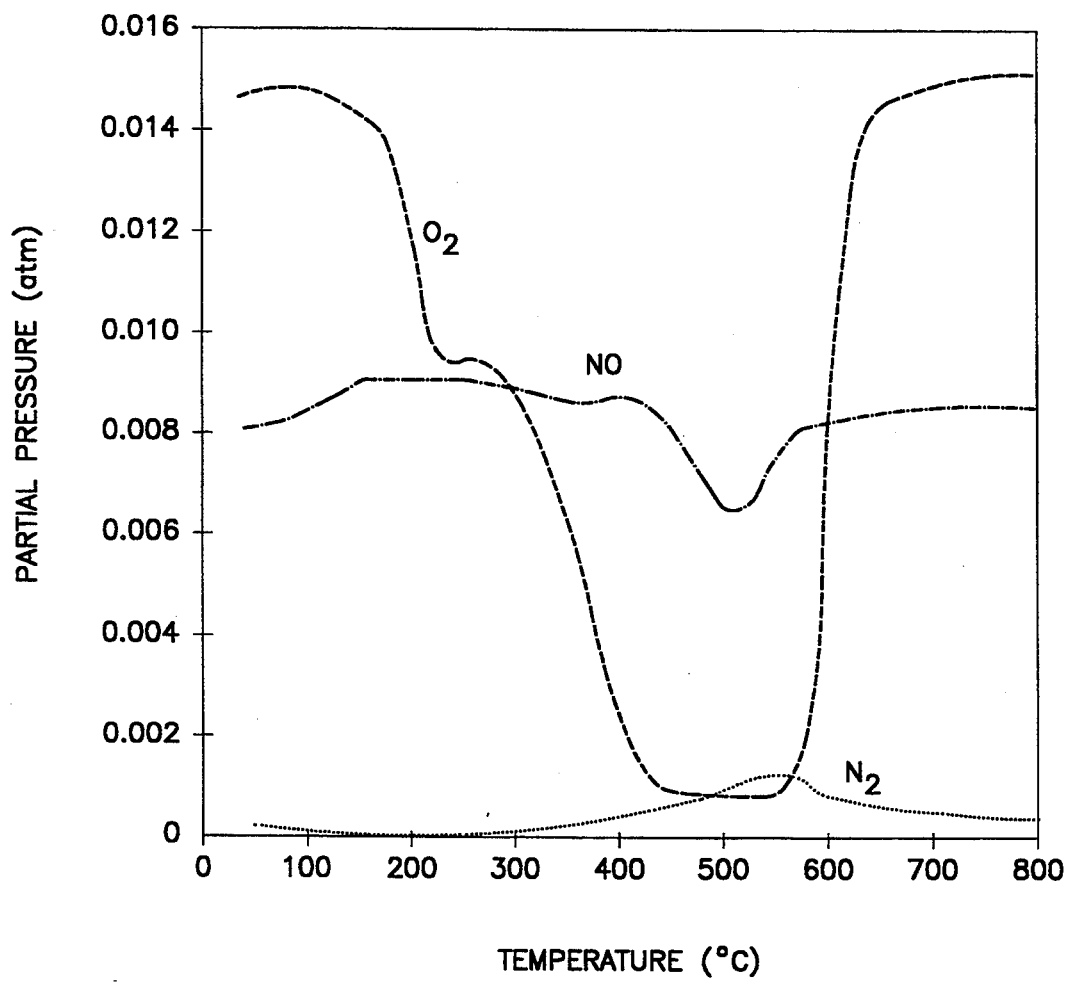
FIG. 3 is a graph of partial pressure versus temperature illustrating a temperature programmed reaction of NO and $O_2$ over reduced $LaNiO_3$.
Figure 4:
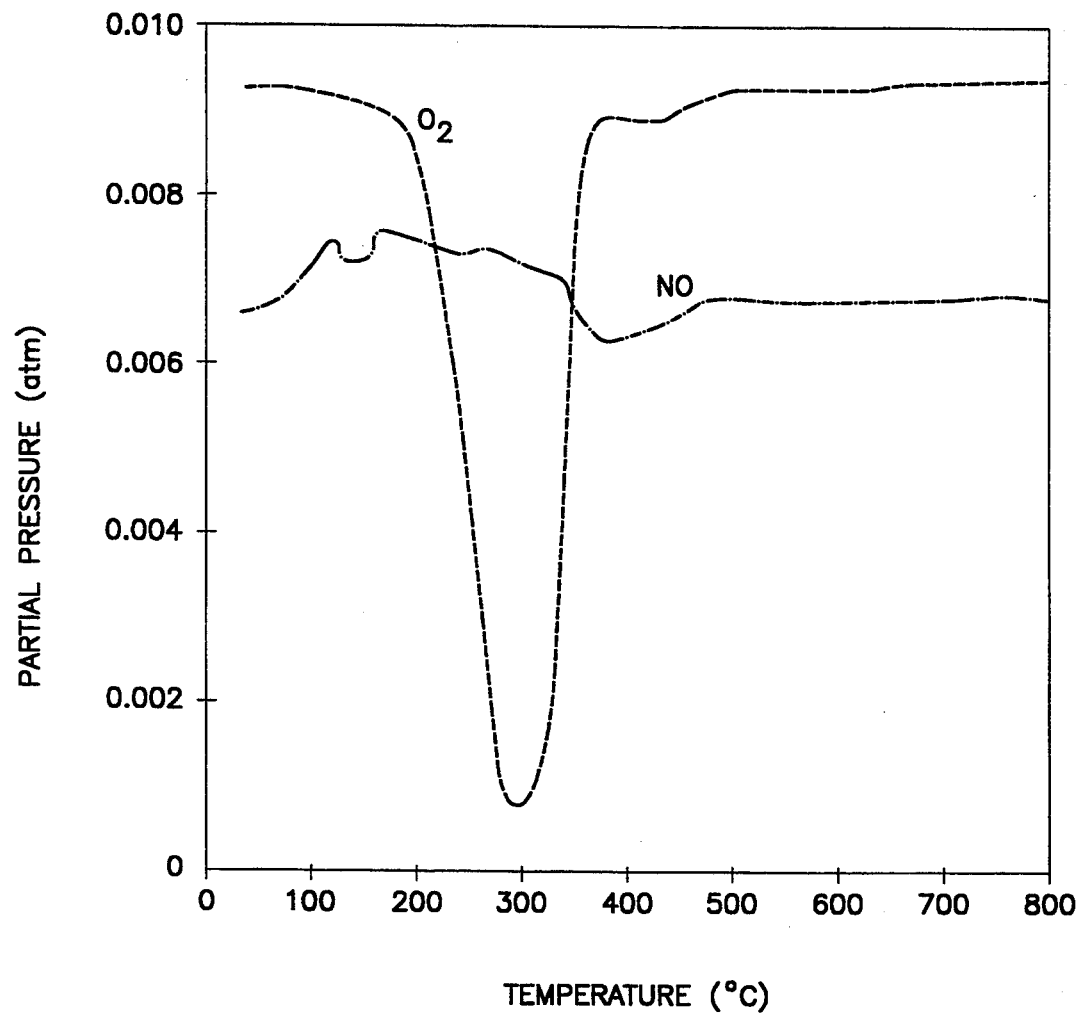
FIG. 4 is a graph of partial pressure versus temperature illustrating a temperature programmed reaction of NO and $O_2$ over reduced $LaFeO_3$.
Figure 5:
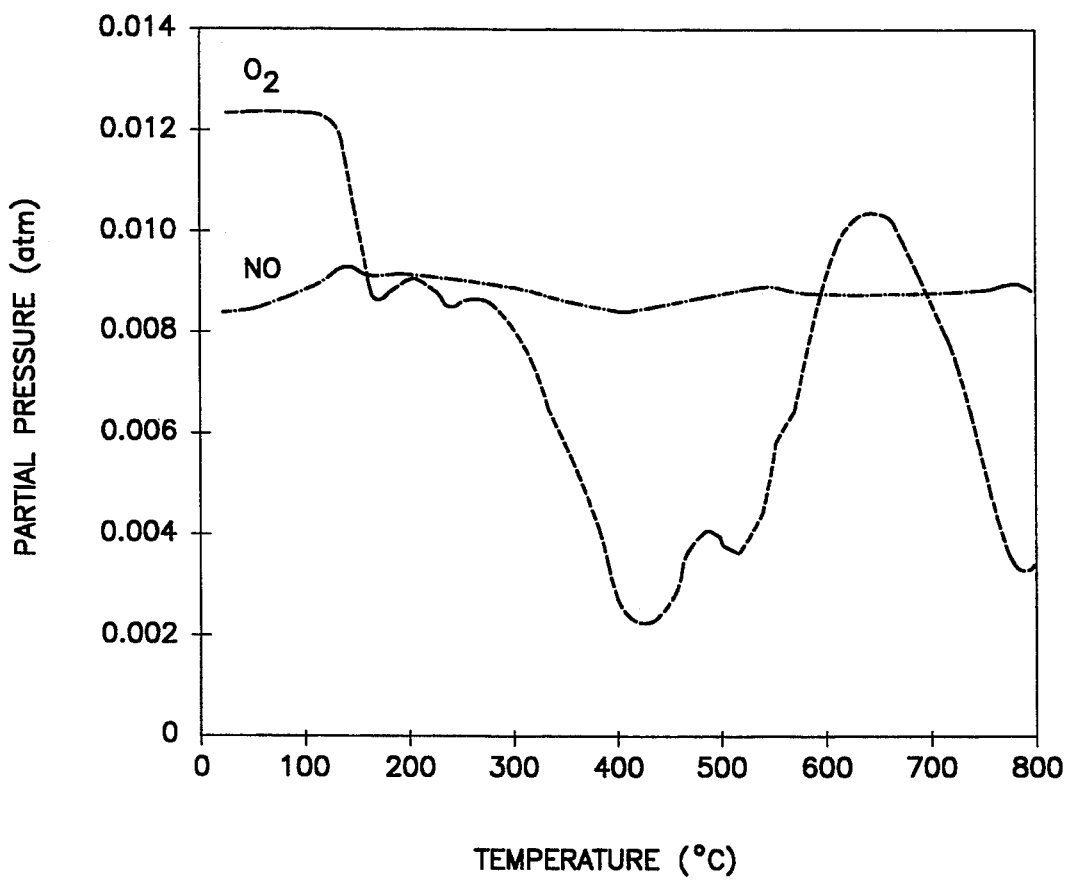
FIG. 5 is a graph of partial pressure versus temperature illustrating a temperature programmed reaction of NO and $O_2$ over reduced $LaCoO_3$.
Figure 6:
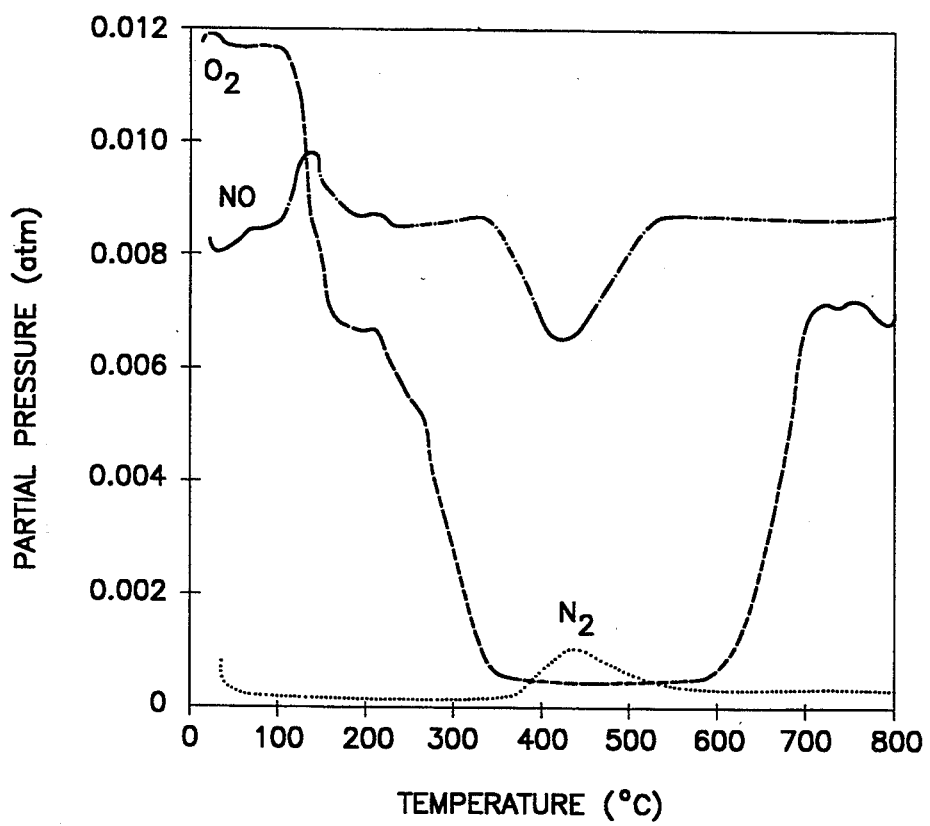
FIG. 6 is a graph of partial pressure versus temperature illustrating a temperature programmed reaction of NO and $O_2$ over reduced $LaMnO_3$.

Specifically, FIGS. 2 through 7 show temperature programmed reactions (TPR) of NO and $O_2$ over reduced $La_2CuO_4$, $LaNiO_3$, $LaFeO_3$, $LaCoO_3$, $LaMnO_3$, and $LaSrCoO_3$, respectively. The foregoing compounds were pre-reduced in a $CO/CO_2$ atmosphere to simulate application of a fixed 0.6 reduction voltage. The TPR of $La_2CuO_4$ in FIG. 2 shows a greater than 99% removal of $O_2$ with only a minimal reduction in NO concentration at high temperature and with minimal formation of $N_2$. The TPR of $LaNiO_3$ in FIG. 3 shows that this compound is selective to $O_2$, although some $N_2$ is formed after the $O_2$ is removed. The TPRs of $LaFeO_3$ in FIG. 4 and $LaCoO_3$ in FIG. 5 show that these compounds exhibit selectivity to $O_2$ with no significant $N_2$ formation, but their activity is not optimum (although usable) relative to complete removal of either $O_2$ or NO. The TPR of $LaSrCoO_3$ in FIG. 6 shows that this compound is relatively selective to $O_2$ as compared to NO.

Comparison of the TPR data of $LaCoO_3$ in FIG. 5 with that of $LaSrCoO_3$ in FIG. 6 shows the effect of substitution of lower valent cations ($Sr^{+2}$ instead of $La^{+3}$) on the A site of the perovskite $ABO_x$. A similar effect would be observed for substitution of $Sr^{+2}$ for $La^{+3}$ in any of the perovskites described herein. In essence, the activity is increased resulting in greater reduction of both $O_2$ and NO. Other possible lower valent cations for this purpose would include, for example but not limited to, calcium ($Ca^{+2}$) and barium ($Ba^{+2}$).

Figure 7:
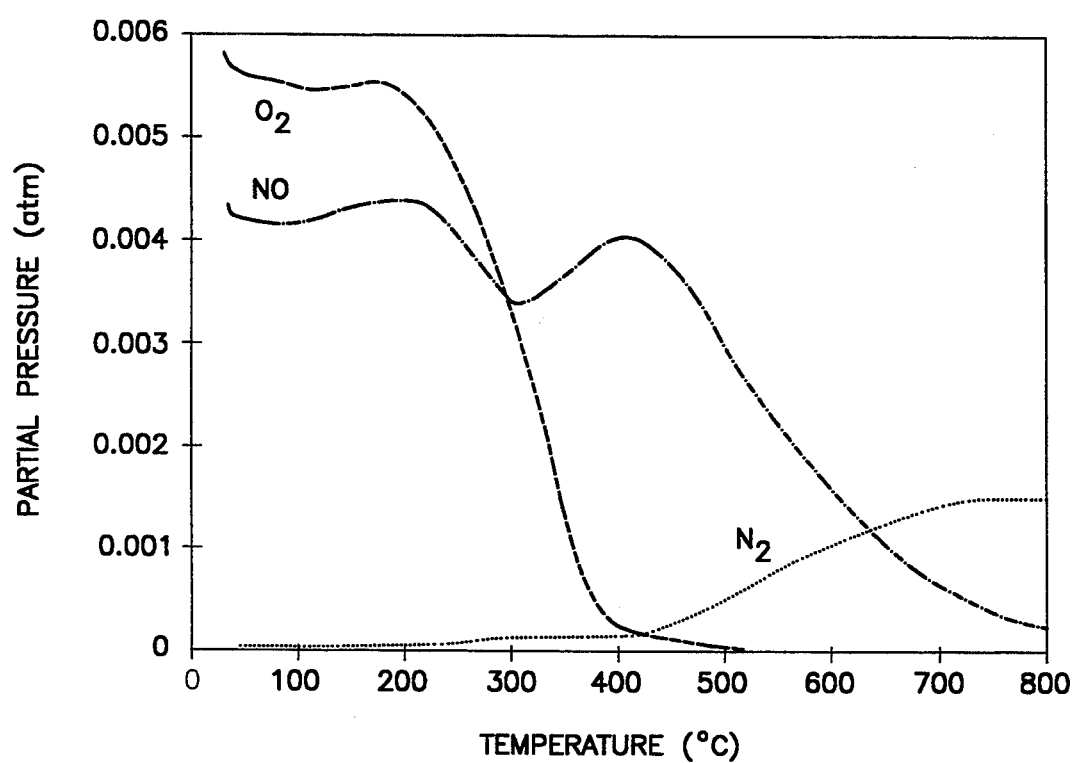
FIG. 7 is a graph of partial pressure versus temperature illustrating a temperature programmed reaction of NO and $O_2$ over reduced $LaSrCoO_3$.
Figure 8:
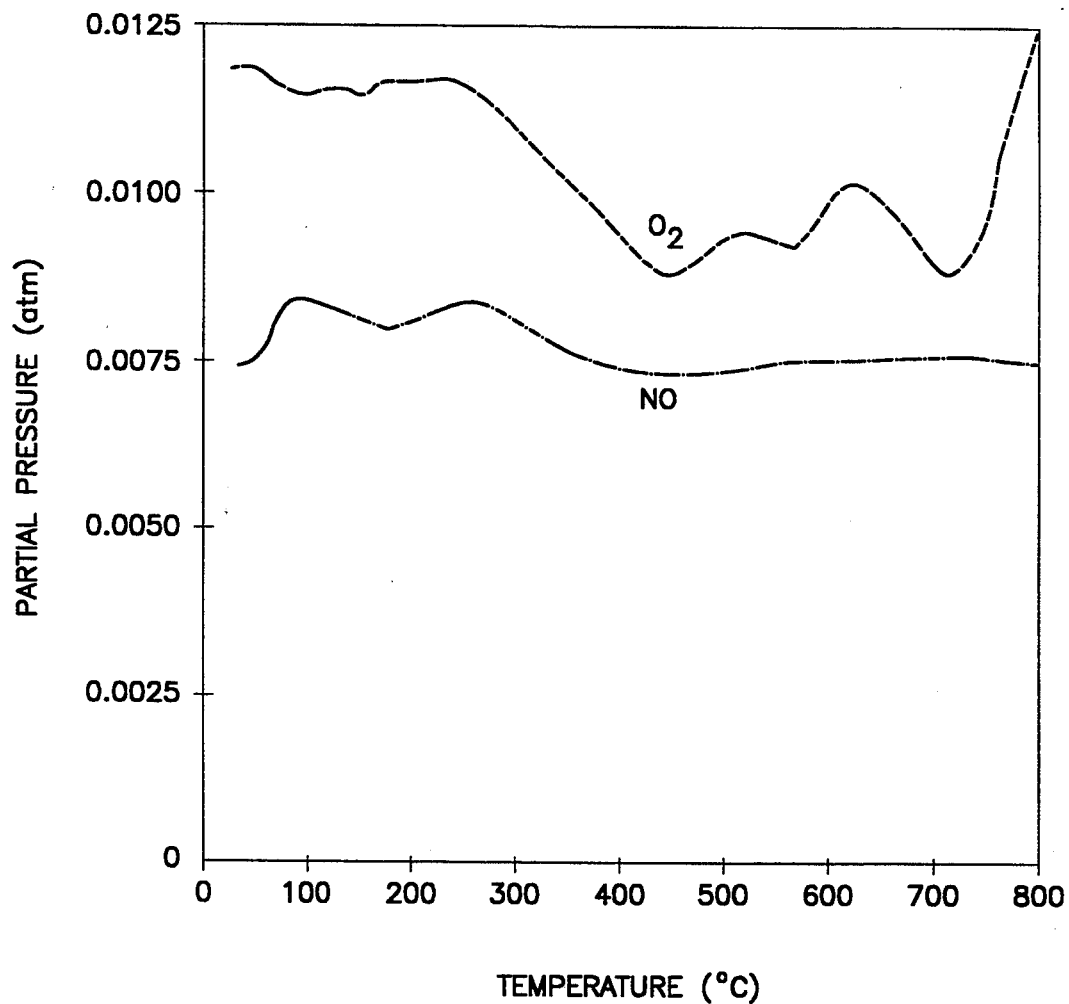
FIG. 8 is a graph of partial pressure versus temperature illustrating a temperature programmed reaction of NO and $O_2$ over reduced $LaRuO_3$.

It was further determined by experimentation that the perovskites lanthanum ruthenium oxide ($LaRuO_3$) and lanthanum manganese oxide ($LaMnO_3$) were both selective and active to $NO_x$, after depletion of $O_2$. These results are illustrated in FIGS. 7 and 8. Specifically, FIGS. 7 and 8 show TPR reactions of NO and $O_2$ over reduced $LaRuO_3$ and $LaMnO_3$, respectively. The foregoing compounds were pre-reduced in a $CO/CO_2$ atmosphere to simulate application of a fixed 0.6 reduction voltage. The TPR of $LaRuO_3$ in FIG. 3 shows an initial reduction in NO concentration concomitant with the onset of significant $O_2$ reduction and then significant reduction in NO concentration at higher temperatures. The TPR of $LaMnO_3$ in FIG. 8 shows that this compound is more selective to NO than to $O_2$ with some $N_2$ formation. The use of the foregoing perovskites and their implementation within the sensor 10 of FIG. 1 is described in further detail hereinafter.

The sensor 10 of FIG. 1 is operated in any of at least three modes of operation, depending upon the selectivity of the materials which are used for each of the internal electrodes 16a, 17a. For the first mode of operation, the electrode 16a comprises $La_2CuO_4$ (most preferred), $LaNiO_3$, $LaFeO_3$, $LaCoO_3$, $LaMnO_3$, or $LaSrCoO_3$ and the electrode 17a comprises $LaRuO_3$ (most preferred) or $LaMnO_3$. This implementation provides for a significant difference in catalytic selectivity and, consequently, a very accurate ultimate determination of $NO_x$ concentration. In this configuration, the electrode 16a is highly selective to $O_2$ in the presence of $O_2$ and $NO_x$, while the electrode 17a is relatively selective to $NO_x$. In this first mode of operation, a power source 18, such as a voltage source or a current source, applies the electrical bias between electrodes 16a, 16b of the first electrochemical cell 16, as shown in FIG. 1, so that $O_2$, not $NO_x$, is consumed at the internal electrode 16a, passes through the electrolyte body 14', and is discharged outside the sensor 10 via the external electrode 16b. The power source 18 induces enough voltage $v_1$ and enough current $i_1$ through the electrolyte body 14' so that substantially all of the $O_2$ in the chamber 12, which is diffusing through the pin-like aperture 15, is eliminated from the chamber 12 with the first electrochemical cell 16, which serves as a pumping cell.

After removal of generally all of the $O_2$ by the electrode 16a, the partial pressure of the remaining gaseous oxide compounds, preferably including $NO_x$, in the chamber 12 causes a voltage $v_2$ to be generated between the internal and external electrodes 17a, 17b of the second electrochemical cell 17, which serves as a sensing cell. The partial pressure of $NO_x$ in the chamber 12 is determined by measuring the voltage $v_2$ across the electrodes 17a, 17b or by measuring the current $i_2$ flowing through the electrolyte body 14''. A suitable detector 21 measures the electrical characteristic, that is, the voltage $v_2$ or the current $i_2$, of the second electrochemical cell 17. In order to measure the current $i_2$, the detector 21 may apply a voltage to enhance $v_2$ to thereby increase $i_2$ to a level where it can easily be measured. In essence, the concentration of $NO_x$ within the chamber 12 is proportional to the current $i_2$ and/or the voltage $v_2$ at the second electrochemical cell 17.

In a second mode of operation, referring again to FIG. 1, the electrode 16a comprises $La_2CuO_4$ (most preferred), $LaNiO_3$, $LaFeO_3$, $LaCoO_3$, $LaMnO_3$, or $LaSrCoO_3$, and the electrode 17a comprises any material, for instance but not limited to, $LaMnO_3$, platinum, rhodium, or another noble metal, which can consume both $NO_x$ and $O_2$, even if the material's selectivity between $O_2$ and $NO_x$ is close. In this configuration, the power source 18, such as a voltage source or a current source, applies the electrical bias $v_1$ between electrodes 16a, 16b of the first electrochemical cell 16 so that $O_2$ is consumed at the $La_2CuO_4$ internal electrode 16a, passes through the electrolyte body 14' thereby generating a current $i_1$, and is discharged outside the sensor 10 via the external electrode 16b.

While the electrode 16a is in operation depleting the $O_2$, the electrode 17a is in operation depleting both $O_2$ and $NO_x$ concurrently. The detector 21 measures the electrical characteristics, either voltages $v_1$, $v_2$ or the currents $i_1$, $i_2$, of the first and second electrochemical cells 16, 17, respectively. The detector 21 measures the electrical characteristics $v_1$, $i_1$, as indicated by phantom lines 22a, 22b in FIG. 1. In essence, the concentration of $NO_x$ within the chamber 12 is proportional to the difference between either the voltages $v_1$, $v_2$ or the currents $i_1$, $i_2$, because $v_1$, $i_1$ depend upon $O_2$ concentration and $v_2$, $i_2$ depend upon the concentration of both $O_2$ and $NO_x$. In addition, as with the first mode of operation, in order to more easily measure the current $i_2$, the detector 21 may apply a voltage to elevate the voltage $v_2$ to thereby increase current $i_2$ to a level where it can be better measured.

In a third mode of operation, with reference again to FIG. 1, the electrode 16a comprises any material, for instance but not limited to, $LaMnO_3$, platinum, which can consume both $NO_x$ and $O_2$, even if the material's selectivity between $O_2$ and $NO_x$ is close, while the electrode 17a comprises $La_2CuO_4$ (most preferred), $LaNiO_3$, $LaFeO_3$, $LaCoO_3$, $LaMnO_3$, or $LaSrCoO_3$. In this configuration, the power source 18, such as a voltage source or a current source, applies the electrical bias $v_1$ between electrodes 16a, 16b of the first electrochemical cell 16 so that $O_2$ and $NO_x$ is concurrently consumed at the internal electrode 16a, are passed through the electrolyte body 14' thereby generating a current $i_1$, and are discharged outside the sensor 10 via the external electrode 16b.

While the electrode 16a is in operation depleting both $O_2$ and $NO_x$, the electrode 17a is in operation depleting generally only $O_2$. The detector 21 measures the electrical characteristics, either voltages $v_1$, $v_2$ or the currents $i_1$, $i_2$, of the first and second electrochemical cells 16, 17, respectively. The detector 21 measures the electrical characteristics $v_1$, $i_1$, as indicated by phantom electrical lines 22a, 22b in FIG. 1. In essence, the concentration of $NO_x$ within the chamber 12 is proportional to the difference between either the voltages $v_1$, $v_2$ or the currents $i_1$, $i_2$, because $v_2$, $i_2$ depend upon $O_2$ concentration and $v_1$, $i_1$ depend upon the concentration of both $O_2$ and $NO_x$. In addition, as with the other modes of operation, in order to more easily measure the current $i_2$, the detector 21 may apply a voltage to elevate the voltage $v_2$ to thereby increase current $i_2$ to a level where it can be better measured.

Figure 9:
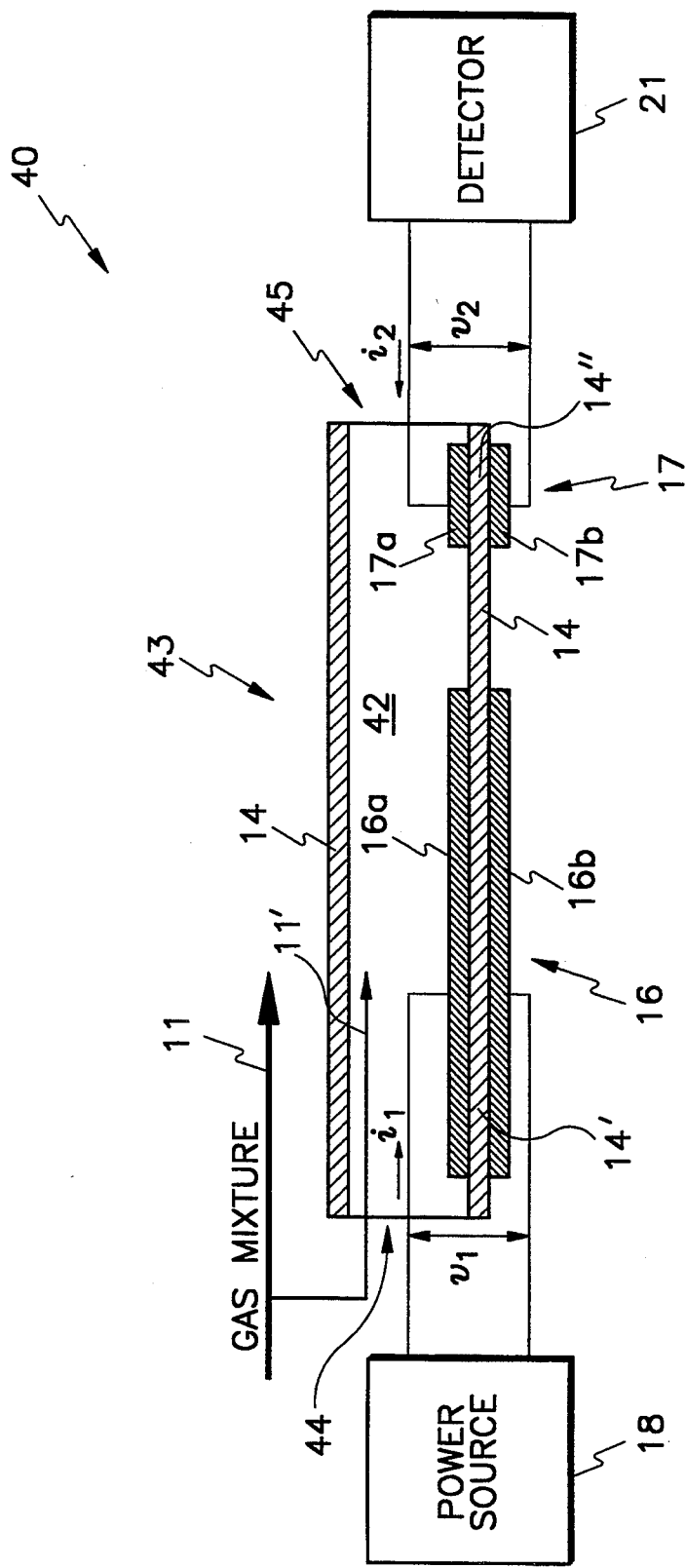
FIG. 9 is a schematic view illustrating a second embodiment of a sensor in accordance with the present invention.

A second embodiment of the present invention is shown in FIG. 9. Referring to FIG. 9, a sensor 40 comprises an elongated chamber 42 defined by an elongated tube-like housing 43 with any cross-sectional geometric shape, but preferably cylindrical. The tube-like housing 43 has a gas mixture inlet 44 for receiving the gas portion 11' of the gas mixture 11 and a gas mixture outlet 45 for expelling the gas portion 11' after passage through the tube-like housing 43. The internal electrodes 16a, 17a of the respective first and second electrochemical cells 16, 17 are disposed within the chamber 42 opposing the respective external electrodes 16b, 17b. The housing 43 is preferably made of the solid electrolyte 14 so that the electrode pairs 16a, 16b and 17a, 17b are separated by corresponding electrolyte bodies 14', 14" at any location along the length of the housing 43.

The sensor 40 of FIG. 9 can be operated in first and second modes of operation, similar to the sensor 10, and with the electrode materials described previously, and therefore, the discussion before relative to sensor 10 is incorporated herein by reference. In each of these configurations and modes of operation, the electrochemical cell for consuming, or pumping, $O_2$ is situated upstream from the electrochemical cell for consuming and sensing the oxide compound. In other words, in the sensor 40, the internal electrode 16a of the first electrochemical cell 16 is always situated in the tube-like housing 43 nearer to the gas mixture inlet 44 than the internal electrode 17a of the second electrochemical cell 17 so that the $O_2$ can be removed from the gas portion 11' by the internal electrode 16a of the first electrochemical cell 16 before the gas portion 11' reaches the internal electrode 17a of the second electrochemical cell 17. In order to further ensure that most of the $O_2$ is removed from the gas mixture 11', the area and/or length of the electrodes 16a, 16b of the first electrochemical cell 16 may be made much larger than the electrodes 17a, 17b of the second electrochemical cell 17, as is illustrated in FIG. 9.

The experimental results indicate that other metal oxide compounds and perovskites, not yet identified, could be used in the electrodes 16a, 17a for selectively measuring the concentration of these other exhaust oxide compounds in the gas mixture within the chambers 12, 42 of respective sensors 10, 40. For instance, it is generally known in the art that oxide compounds, particularly $CO_x$, can be removed when higher voltages are applied across electrolytic bodies as compared with $O_2$ and $NO_x$. Consequently, it is envisioned that other metal oxide compounds can be derived for selectively sensing and/or consuming other specific oxide compounds, including $CO_x$, while in the presence of $O_2$.

Furthermore, in each of the sensors 10, 40, after removal of $O_2$ and $NO_x$ from the exhaust 11', compounds such as $CO_x$, $SO_x$, and $H_2O$ generally remain. The sensors 10, 40 of respective FIGS. 1 and 9 may be modified to sense more than one oxide compound passing in the chambers 12, 42. In these further embodiments, an additional sensing electrochemical cell(s) would be positioned in the respective chambers 12, 42 and would be selective to an additional oxide compound(s). In the sensor 10, the additional sensing electrochemical cell(s) could be positioned anywhere within the chamber 12 adjacent the first and second electrochemical cells 16, 17. In the sensor 40, the additional sensing electrochemical cell(s), selective to another oxide compound, would be situated on the tube-like housing 43 downstream from the second electrochemical cell 17, that is, nearer the outlet 45. The ability to discriminate between gaseous oxides is made possible by a distinct difference in relative catalytic selectivity of the internal electrodes on the chamber side of the sensors 10, 40. In these embodiments, each of the additional sensing electrochemical cells would have its own respective detector 21, or an equivalent thereof.

It will be apparent to one of skill in the art that many variations and modifications may be made to the preferred embodiments as described above without substantially departing from the principles of the present invention. All such variations and modifications are intended to be included herein and within the scope of the present invention, as set forth in the following claims.

Wherefore, the following is claimed:

1. A sensor for accurately measuring a concentration of an oxide compound in a gas mixture, comprising:
   a chamber adapted to receive the gas mixture;
   a first cell means comprising a first internal electrode inside said chamber, a first external electrode outside said chamber, and a first electrolyte body therebetween, said first electrolyte body is substantially permeable to oxygen ions when said first electrolyte body is electrically biased during operation of the sensor, said first internal electrode comprising a perovskite having selectivity to reduce oxygen and, not the oxide compound, in said chamber; and
   a second cell means comprising a second internal electrode inside said chamber, a second external electrode outside said chamber, and a second electrolyte body therebetween, said second electrolyte body is substantially permeable to said oxygen ions when said second electrolyte body is electrically biased during operation of the sensor, said second internal electrode comprising a metal oxide having selectivity to reduce the oxide compound in said chamber after depletion of the oxygen within said chamber;
   whereby an electrical characteristic associated with said second cell means corresponds to the concentration of the oxide compound in the gas mixture.

2. The sensor of claim 1, wherein said chamber comprises an enclosure for housing said internal electrodes and an elongated aperture in the shape of a pin through which the gas mixture enters said enclosure.

3. The sensor of claim 1, wherein said chamber comprises an elongated enclosure in the shape of a tube for housing said internal electrodes, said enclosure having first and second apertures for receiving and expelling the gas mixture respectively, said first and second internal electrodes disposed in succession along an axis connecting said first and second apertures, said first internal electrode disposed along said axis between said first aperture and said second internal electrode.

4. The sensor of claim 1, wherein said second internal electrode comprises a perovskite.

5. The sensor of claim 4, wherein said perovskite is selected from the group consisting of $LaRuO_3$ and $LaMnO_3$.

6. The sensor of claim 1, wherein said first and second electrolyte bodies are portions of a singular wall of said chamber.

7. The sensor of claim 1, wherein said first and second electrolyte bodies comprise zirconia.

8. The sensor of claim 1, wherein said perovskite is selected from the group consisting of $La_2CuO_4$, $LaNiO_3$, $LaFeO_3$, $LaCoO_3$, $LaMnO_3$, and $LaSrCoO_3$.

9. A sensor for accurately measuring a concentration of an oxide compound in a gas mixture, comprising:
   a chamber adapted to receive the gas mixture;
   a first cell means comprising a first internal electrode inside said chamber, a first external electrode outside said chamber, and a first electrolyte body therebetween, said first electrolyte body is substantially permeable to oxygen ions when said first electrolyte body is electrically biased during operation of the sensor, said first internal electrode comprising a perovskite having selectivity to reduce the oxygen and, not the oxide compound; and
   a second cell means comprising a second internal electrode inside said chamber, a second external electrode outside said chamber, and a second electrolyte body therebetween, said second electrolyte body is permeable to said oxygen ions when said second electrolyte body is electrically biased during operation of the sensor, said second internal electrode comprising a material having selectivity to concurrently reduce both the oxygen and the oxide compound;
   whereby first and second electrical characteristics associated with said first and second cell means are measured and the concentration of the oxide compound in the gas mixture is determined by mathematically combining said first and second electrical characteristics.

10. The sensor of claim 9, wherein said chamber comprises an enclosure for housing said internal electrodes and an elongated aperture in the shape of a pin through which the gas mixture enters said enclosure.

11. The sensor of claim 9, wherein said chamber comprises an elongated enclosure in the shape of a tube for housing said internal electrodes, said enclosure having first and second apertures for receiving and expelling the gas mixture respectively, said first and second internal electrodes disposed in succession along an axis connecting said first and second apertures, said first internal electrode disposed along said axis between said first aperture and said second internal electrode.

12. The sensor of claim 9, wherein said second internal electrode is a perovskite.

13. The sensor of claim 12, wherein said perovskite is selected from the group consisting of $LaRuO_3$ and $LaMnO_3$.

14. The sensor of claim 9, wherein said first and second electrolyte bodies are portions of a singular wall of said chamber.

15. The sensor of claim 9, wherein said first and second electrolyte bodies comprise zirconia.

16. The sensor of claim 9, wherein said perovskite is selected from the group consisting of $La_2CuO_4$, $LaNiO_3$, $LaFeO_3$, $LaCoO_3$, $LaMnO_3$, and $LaSrCoO_3$.

17. The sensor of claim 9, wherein said second internal electrode is selected from the group consisting of Pt and Rh.

18. The sensor of claim 9, wherein said second internal electrode comprises a perovskite selected from the group consisting of $LaRuO_3$ and $LaMnO_3$.

19. A method for accurately measuring a concentration of an oxide compound in a gas mixture, comprising the steps of:
   exposing the gas mixture to a first internal electrode comprising a perovskite and a second internal electrode comprising a metal oxide;
   selectively reducing the oxygen with said first internal electrode without substantially depleting the oxide compound in the gas mixture;
   reducing the oxide compound with said second internal electrode after said first internal electrode depletes the oxygen; and
   measuring electrical characteristic associated with said second internal electrode to determine the concentration of the oxide compound in the gas mixture.

20. The method of claim 19, further comprising the steps of:
   measuring the electrical current between said first internal electrode and a first external electrode;
   measuring the electrical current between said second internal electrode and a second external electrode.

21. The method of claim 19, further comprising the steps of:
   measuring the voltage between said first internal electrode and a first external electrode;
   measuring the voltage between said second internal electrode and a second external electrode.

22. The method of claim 19, wherein the oxide compound is $NO_x$.

23. A method for accurately measuring a concentration of an oxide compound in a gas mixture, comprising the steps of:
   exposing the gas mixture to first internal and second internal electrodes, said first electrode comprising a perovskite;
   selectively reducing the oxygen with said first internal electrode without substantially depleting the oxide compound in the gas mixture;
   reducing both the oxygen and the oxide compound with said second internal electrode;
   measuring first and second electrical characteristics associated with said first internal and second internal electrodes respectively; and
   determining the concentration of the oxide compound in the gas mixture by mathematically combining said first and second electrical characteristics.

24. The method of claim 23, further comprising the steps of:
   measuring the electrical current between said first internal electrode and a first external electrode;
   measuring the electrical current between said second internal electrode and a second external electrode.

25. The method of claim 23, further comprising the steps of:
   measuring the voltage between said first internal electrode and a first external electrode;
   measuring the voltage between said second internal electrode and a second external electrode.

26. The method of claim 23, wherein the oxide compound is $NO_x$.

* * * * *